United States Patent [19]
Zahn

[11] Patent Number: 4,634,380
[45] Date of Patent: Jan. 6, 1987

[54] NON-FLOATING TECHNIQUE-MALE

[76] Inventor: Eric H. Zahn, P.O. Box 3434, Bellevue, Wash. 98009

[21] Appl. No.: 689,316

[22] Filed: Jan. 7, 1985

[51] Int. Cl.⁴ .............................................. A61C 13/12
[52] U.S. Cl. ..................................... 433/181; 433/213
[58] Field of Search ............... 433/181, 182, 183, 180, 433/171, 213

[56] References Cited
U.S. PATENT DOCUMENTS 2,611,957  9/1952  Baca et al. ......................... 433/170
3,023,500  3/1962  Prosen ................................ 433/213
3,344,842  10/1967 Cameron ............................. 433/181
4,272,241  6/1981  Crisalli .............................. 433/171
4,474,499  10/1984 Pedrazzini .......................... 433/213

Primary Examiner—John J. Wilson
Attorney, Agent, or Firm—Garrison & Stratton

[57] ABSTRACT

Dental and other intricate technique-models to be invested in compatible plastic material have a reduced tendency to float through the association herewith of a foreign body that increases the relative weight of the model as compared with the investment material.

19 Claims, 7 Drawing Figures

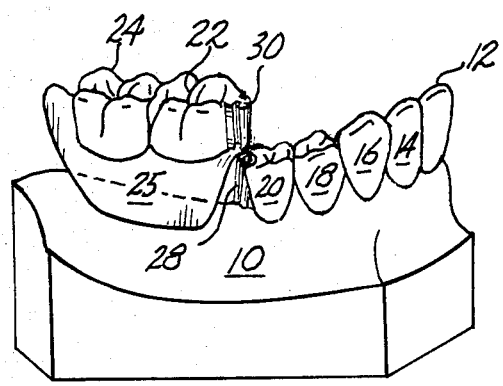
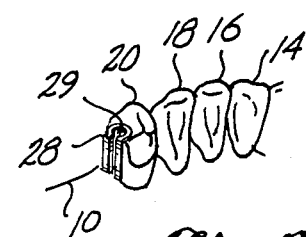
Fig.1.
Fig.2.
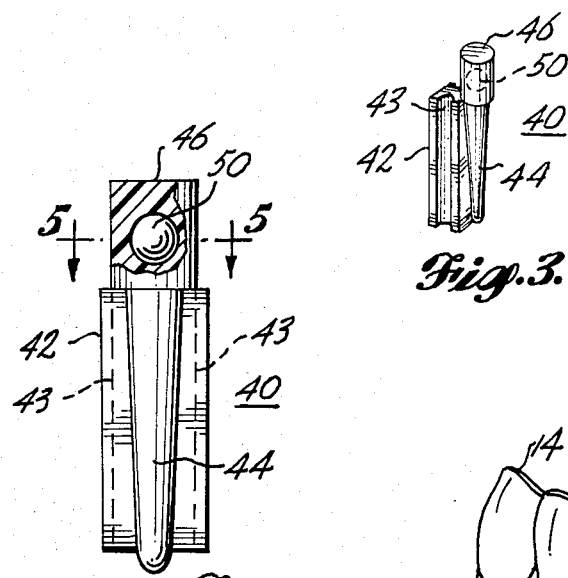
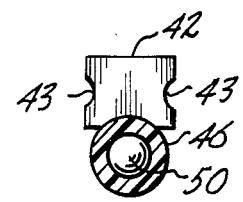
Fig.3.
Fig.5.
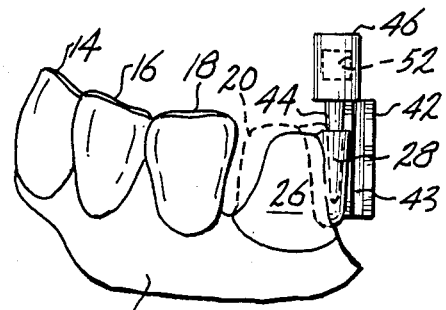
Fig.4.
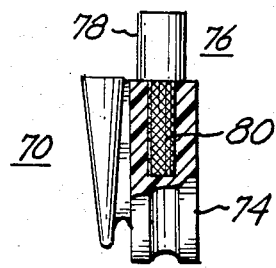
Fig.6.
Fig.7.

NON-FLOATING TECHNIQUE-MALE

BACKGROUND OF INVENTION

In the production of precision attachment members, particularly male members as employed in intracoronal precision attachments and in segmented dental bridgework, considerable difficulty has been encountered when certain attachment-forming elements are being invested in colloidal investment material having a similar, if not identical specific gravity. The difficulty is often encountered where the attachment elements and the investment materials are dental alginate impression products. Under such circumstances, pre-formed attachment-forming elements have tended to "float" in the investment material and, thus, become dislocated or mispositioned. This defeats the production of precision castings being sought as is always the case in the dental restoration field.

SUMMARY OF THE INVENTION

The invention supplies a solution to the "float" problem. This is accomplished by associating with a flexible, preformed, rubber-like technique-male used in producing the precision attachment, a foreign body having such a weight as to decrease or eliminate the tendency of technique-male to float in compatible investment material in which during processing it is embodied.

DESCRIPTION OF THE DRAWINGS

FIG. 1 is an exploded perspective view of a portion of a dental model, commonly employed in the fabrication of precision attachments to removable partial dentures, illustrating the male/female attachment principle;

FIG. 2 is a detailed perspective view of a female attachment cavity supported by a replica tooth;

FIG. 3 is a perspective of a preformed technique-male attachment member;

FIG. 4 is an upright enlarged view of a preformed technique-male attachment member with a portion broken away to reveal the foreign body associated therewith;

FIG. 5 is a cross-sectional view in the plane 5—5 of FIG. 4;

FIG. 6 is a side view of a portion of a dental model showing an alternate form of technique-male, rubber-like attachment-former in place in a female attachment cavity previously formed on a coping; and FIG. 7 shows an alternate form of technique-male embodying the invention herein.

SPECIFICATIONS

In FIG. 1, dental model 10 has reproduction teeth 12, 14, 16, 18 and 20 secured upright therein. In this instance, the dental mandiblar prosthesis comprising teeth 22 and 24, on saddle 25 as shown, is to be attached to replica tooth 20. Usually a lingual bar extends transversely from saddle 25 to a similar saddle or clasp fitting (not shown) that serves to stabilize the restoration in the mouth. A female attachment cavity member 28 is incorporated in the replica tooth 20 and the interfitting technique-male portion 30 slides therein. The cavity 29 of member 28 as shown in FIG. 2 converges or decreases downward. The technique-male portion 30 is tapered to match tapered cavity 28 and, when reproduced, produces the male element that is removably inserted into the female cavity of replica tooth 20 when the prothesis is in place in the patient's mouth.

This invention is primarily concerned with the accurate production of a technique-male attachment-former portion 30 for use in producing removable partial dentures and related prosthetic appliances. A first step in the procedure is the manufacture of male-technique model 40 as shown in FIGS. 3, 4 and 5. Male 40 is molded or cast of a material selected from one of the silicone rubber or other rubber-like, elastic materials that are form-retaining when cured and, faithfully duplicate intricate shapes while remaining flexible or elastic.

Model 40 comprises base block 42 having side wall concavities 43 and supporting tapered attachment-forming element 44 upright on the front face. Tapered mold element 44 is surmounted by head 46 which rises above block 42. The block 42, attachment-forming element 44 and head 46 may be cast or molded as an integral model preferably of a flexible silicone rubber material of the types well-known in and commonly used in the field and art of dental reproductions. The concavities 43 on the sides of block 42 insure joinder between block 42 and the duplicating material in which it is later invested.

The foreign body, associated with the technique-male 40, is usually placed within head 46. It may take the form of a metallic sphere 50 as shown in FIGS. 3, 4 and 5 or, alternatively, the shape of a metallic slug or cylinder 52 as seen in FIG. 6. Shape is a matter of choice. The main function of the foreign body is to increase the weight of the technique-male 40 relative similar duplicating or investment materials in which it is later embodied. This reduces the tendency of the technique-male to float out of place during investment procedures while the duplicating material is fluid or in the process of solidifying.

In the drawings the disposition of the tapered male attachment-forming element has been downward since this is probably the most common use of the weighted elastic silicone male. However, as is well known to those skilled in the art of producing fine dental restorations, occasions will arise when it will be desirable that a female socket or cavity, similar to 28 of FIG. 2, would be disposed upended and assembled with an attachment pin, likewise upended. In such case the removable dental part could include the female socket.

The technique-male 70 of FIG. 7 has male attachment forming element 44 at one side of base block 74. The foreign body 76 is mounted on block 74 in an axis to one side of the axis of element 44. Body 76 has the head 78 surmounting stem 80 which is buried in block 74. Stem 80 may be knurled to aid retention in the flexible silicone of which the technique-male 70 is formed.

To impart an appreciation of the delicate nature and size of the technique-male shown in FIG. 3, one such block 42 is about ¼" long, pin-forming member 44 about 7/64" long and head 46 having a diameter of about ⅛" encases a metal shot 50 about 1/16" in diameter.

It will be apparent to persons skilled in the pertinent art that the system or technique disclosed herein may be used in many dental techniques involving, for example, the production of extra coronal attachments.

It will be understood that the invention disclosed herein may take varied forms differing slightly from the preferred embodiment set forth. All such variations and modifications as fall within the competance of the usual artisan in the pertinent art field is intended to be embraced by the following claims, interpreted as they must be with due regard to the appropriate application of the "doctrine of equivalents" as to scope.

What is claimed is:

1. An improved method of fabrication of a dental attachment for removable partial dentures wherein a replica tooth in place in a patient's model supports an upright female cavity in which is to be seated an elastic technique-male and the same as well as the model is to be invested in a duplicating material having a specific gravity such that said technique-male tends to float out of said female cavity during the investment procedure, the improvement, comprising pre-fabricating said technique-male of a rubber-like substance weighing down said technique-male with a foreign body having such weight that the tendency of said male to float in duplicating material is substantially eliminated and investing said duplicate material.

2. The improvement of claim 1 in which the foreign body is encased within said technique-male.

3. The improvement of claim 1 in which the foreign body is metallic.

4. The improvement of claim 3 in which the foreign body is a metallic sphere.

5. The improvement of claim 4 in which said metallic sphere is a lead shot.

6. The improvement of claim 1 in which the foreign body is disposed in an axis offset from the axis of silicone technique-male.

7. The improvement of claim 1 in which the foreign body is embedded in a technique-male formed of a silicone investment material.

8. A male-technique molded of a rubber-like elastomer that is form-retaining when cured and faithfully duplicates intricate shapes while remaining flexible, to be attached to a vertical downwardly tapered female cavity for a removable partial denture restoration comprising:

a base block;

a pair of concavities located vertically along the sides of said base block;

a supporting attachment member matchingly tapered to be received by said female cavity integrally molded vertically into the forward face of said base block;

a head surmounted upon the base block and the attachment member joining said base block and attachment member into an integral unit;

a foreign body of a density greater than the molded material comprising the block, attachment member and head, integrally molded therein.

9. The male-technique as described in claim 8 where said foreign body is embedded within the head.

10. The male-technique as described in claim 8 where said foreign body is metallic.

11. The male-technique as described in claim 8 where said foreign body is a metallic sphere.

12. The male-technique as described in claim 8 where said foreign body is a lead shot sphere.

13. The male-technique as described in claim 8 where said foreign body is stainless steel sphere.

14. In an improved male-technique molded of a rubber-like elastomer that is form-retaining when cured and flexible to be attached to an upright downwardly tapered female cavity for a removable partial denture restoration having a base block, a pair of concavities located vertically along the sides of said base block, a supporting attachment member matchingly tapered to be received by said female cavity integrally molded vertically into the forward face of said base block, a head surmounted upon the base block and the attachment member joining said base block and attachment member into an integral unit, wherein the improvement comprises:

a foreign body molded into the head of said male-technique, the foreign body having a density greater than the molded material comprising the block, attachment member and head.

15. The male-technique as described in claim 14 where said foreign body is embedded within the head.

16. The male-technique as described in claim 14 where said foreign body is metallic.

17. The male-technique as described in claim 14 where said foreign body is a metallic sphere.

18. The male-technique as described in claim 14 where said foreign body is a lead shot sphere.

19. The male-technique as described in claim 14 where said foreign body is stainless steel sphere.

* * * * *